United States Patent [19]

Becker et al.

[11] Patent Number: 4,688,437
[45] Date of Patent: Aug. 25, 1987

[54] ELECTRODE HOLDER ASSEMBLY

[75] Inventors: David Becker, Brookline; Mark Gelo, Concord, both of Mass.

[73] Assignee: Orion Research, Inc., Cambridge, Mass.

[21] Appl. No.: 837,396

[22] Filed: Mar. 7, 1986

[51] Int. Cl.⁴ .............................................. C25D 17/00
[52] U.S. Cl. ................................................... 73/866.5
[58] Field of Search ................ 73/866.5; 324/446, 447, 324/448, 449, 439, 438; 204/197, 209, 225, 197 R; 74/424.8 A, 409, 441

[56] References Cited

U.S. PATENT DOCUMENTS

| | | | |
|---|---|---|---|
| 3,505,197 | 4/1970 | Malk et al. | 324/447 |
| 3,892,652 | 7/1975 | Levine et al. | 324/438 |
| 4,109,628 | 8/1978 | Miller et al. | 74/441 |
| 4,249,426 | 2/1981 | Erikson et al. | 74/424.8 A |
| 4,392,757 | 7/1983 | Denny et al. | 74/424.8 A |
| 4,414,070 | 11/1983 | Spence | 204/225 |
| 4,459,190 | 7/1984 | Inoue | 204/225 |
| 4,589,298 | 5/1986 | Meyer et al. | 74/409 |

FOREIGN PATENT DOCUMENTS 2918641 11/1980 Fed. Rep. of Germany ..... 74/424.8 A

Primary Examiner—Stewart J. Levy
Assistant Examiner—Robert R. Raevis
Attorney, Agent, or Firm—Cesari and McKenna

[57] ABSTRACT

An electrode holder assembly is provided for holding test electrodes in a sample container. The assembly comprises a vertically aligned lead screw mounted to rotate freely, and a nut, inserted over the lead screw, adapted to move freely over the length of the lead screw when subject to a vertical force. A collet that extends upward from the nut body is biased inwardly by a spring so as to secure a friction fit, substantially free of any backlash movement, between the nut and the lead. Attached to the nut is an electrode holder platform having mounting bores adapted for securing test electrodes therethrough. This assembly allows the test electrodes to be moved up or down, for insertion and removal from a test solution, by one-handed vertical activation of the electrode holder platform. The lead screw, nut, and associated components may all be housed in a tower assembly so that only the electrode platform is exposed.

7 Claims, 3 Drawing Figures

ELECTRODE HOLDER ASSEMBLY

FIELD OF THE INVENTION

The invention relates an electrode holder assembly, and particularly comprises an electrode holder assembly, for supporting test probes, that can be moved vertically with minimal efort.

BACKGROUND OF THE INVENTION

Electrode holder assemblies are often seen in chemical laboratories and other locations where it is necessary to perform either qualitative or quantitative analyses on various sample solutions or substances. The assemblies are used to support one or more test probes or electrodes that are immersed in a sample of a substance in order to obtain a desired analytic test parameter from the substance. An example of such probes is a pH meter test electrode that is used to find the H+ ion concentration of a sample.

In most test situations it is necessary to make measurements of a large number of sample solutions. This necessitates repeatedly inserting a test electrode into a sample container, taking a measurement, removing the electrode, and inserting it into the next container of sample solution.

Currently, there are three types of electrode holder assemblies in general use: platform holders having platforms adjustably mounted on vertical support rods, holders that are supported directly on the sample containers; and platform holders attached to articulated arms. None of these designs provides for simple vertical movement of the test electrodes so that they can be inserted and removed from the sample containers with only minimal effort.

Electrode holders attached to vertical support rods are a very common type of test probe support. These assemblies comprise a vertical support rod secured to a base, a platform adjustably supported on the rod by a thumb-screw clamp and in turn carrying the test electrodes. To raise and lower the platform it is necessary to turn the thumb screw to release the clamp, move the platform to the new height, and reset the thumb screw. When test electrodes are attached to the platform, the operator must use extra care to insure that when the platform clamp is loosened, the platform does not fall. This usually requires the use of two hands to adjust the position of the electrodes, one to manipulate the clamp, and the other to support the platform when it is non-clamped from the support rod. If the test probes are being used to test a succession of samples, the operator must spend considerable time manipulating the clamp and raising and lowering the platform so the successive sample containers can be placed underneath the platform.

A platform holder is a platform, with proberestraining bores through which test probes are inserted. The platform is placed over a sample container so that it rests directly on the rim of the container. To perform analyses on successive samples it is necessary to lift the platform with the probes from the first sample container, place the next sample container within reach of the platform and place the platform on the second sample container. Since the probes are often fragile, it is generally necessary to hold the platform while changing sample containers so as to prevent the electrodes from striking a hard surface and being damaged.

Articulated arms have been provided for the raising and lowering of electrodes. These arms, usually having one or two rods hinged with an electrode platform pivotally attached to the end of one rod so as continually to be horizontally aligned, have their own disadvantages.

To provide an arm with a sufficient range of motion, and yet maintain sufficient stability, the base must be large. Moreover, in a laboratory, where it is desirable to have all necessary equipment close at hand, and where space may be at a premium, working around such an arm may be difficult.

A need therefore exists for an electrode holder assembly that allows test electrodes to be accurately positioned in and removed from a sample container with minimal effort and without interfering with other equipment or other tasks being performed by the operator.

SUMMARY OF THE INVENTION

The invention comprises an electrode holder assembly having a lead screw vertically secured to a base and adapted to rotate freely, and a nut, from which an electrode platform extends, mounted on the lead screw. The nut and lead screw are of such design that, in the absence of an externally applied force, the friction between the two is sufficient to hold the nut and platform combination in position. At the same time, the friction force and the pitch of the lead screw are such that the height of the platform may be freely adjusted up or down by applying a vertical force on the platform, in either direction. This force causes the lead screw to turn, and the platform to move in the direction of the applied force. Thus, the platform, with electrodes inserted therethrough, can be moved up and down with a simple one-handed movement.

In the preferred embodiment of the invention, the nut and lead-screw are provided with an anti-backlash arrangement so as to substantially eliminate hysteresis and thereby facilitate accurate vertical positioning of the platform.

In the preferred embodiment of this invention, backlash elimination is provided by a collet on the nut that is squeezed on the lead screw. The squeezing force is variable and this allows the friction between the nut and lead screw to be adjusted to accomodate for operator preference, or so the assembly can be used with different electrodes of differing weights.

BRIEF DESCRIPTION OF THE DRAWINGS

The foregoing and other features and advantages of the invvention will be apparent from the following more particular description of the preferred embodiment of the invention, as illustrated in the accompanying drawings, in which like characters refer to the same parts throughout the different views. The drawings are not necessarily to scale, emphasis instead being placed upon illustrating the principles of invention

DETAILED DESCRIPTION OF THE PREFERRED EMBODIMENTS

Figure 1:
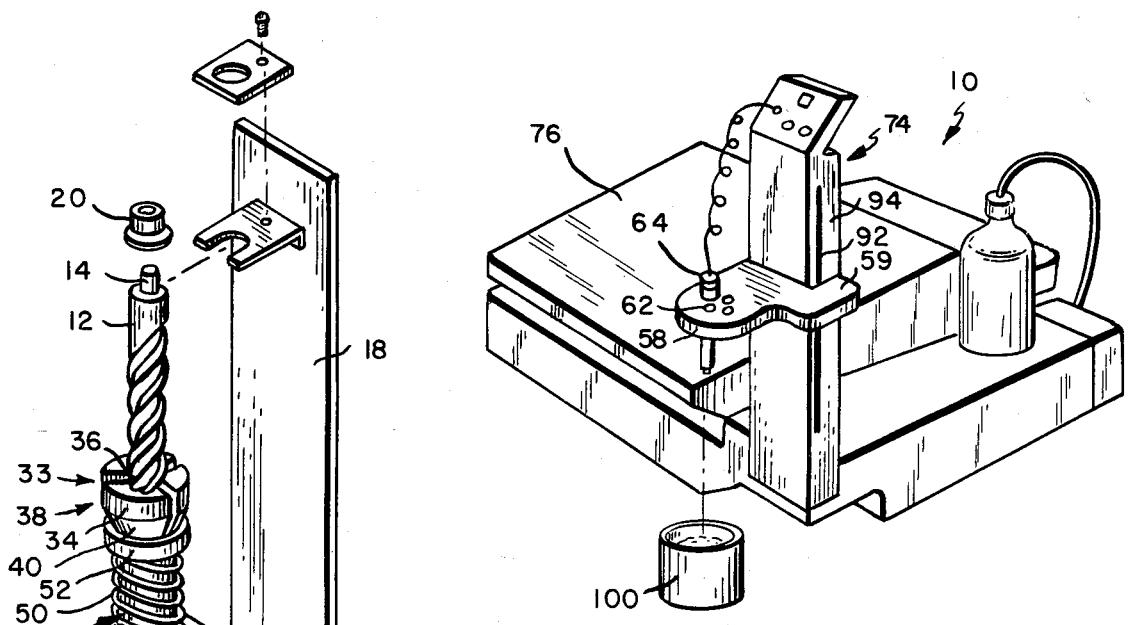
FIG. 1 is perspective view of the electrode holder of this invention housed in a tower associated with an analytical instruement.

As is shown in FIG. 1, electrode holder assembly 10 of this invention comprises a tower 74. The tower 74 is attached to an analytical instrument 76 that also serves as a base for the tower. The assembly 10 also includes an electrode platform 58 that abuts the tower front wall 90. The platform 58 is supported from the tower 74 by a rearward extending mounting arm 59 that is coupled to the inside of the tower through an elongated vertical slot 92 located in the tower side wall 94 as described below.

The electrode platform 58 is supported by the tower 74 in such a manner that its position along the tower can be hand adjusted, and once adjusted will remain at a set height. The platform 58 is provided with a number of retaining bores 62 for inserting electrodes therethrough. A single electrode 64 is shown in the drawing. A sample container 100, containing a volume of liquid to be analyzed, is disposed under the electrode platform so that by moving the platform up and down the electrode 64 can be inserted into and removed from the sample container.

Figure 2:
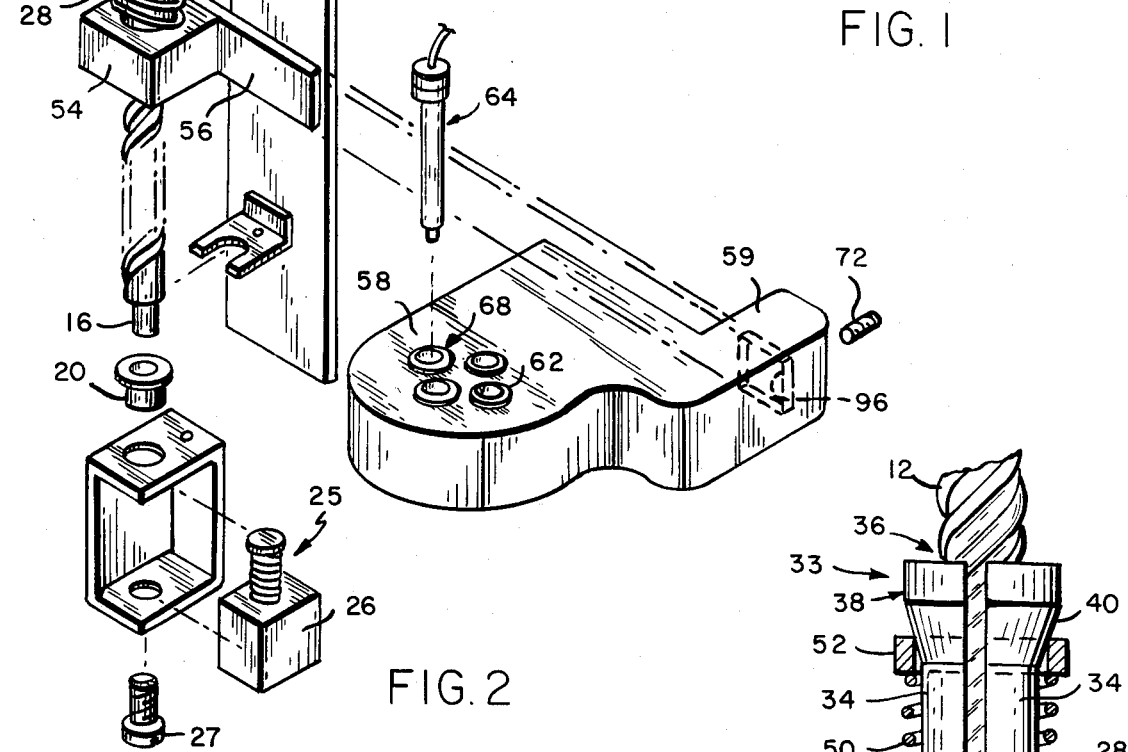
FIG. 2 is an expanded disassembled view of a preferred embodiment of the electrode holder of this invention.

As is seen in FIG. 2, the electrode holder assembly 10 further comprises a threaded lead screw 12 with top and bottom ends 14, 16 of reduced diameter. The lead screw is mounted to a frame 18 which is the inside of the back wall of the tower. Bearing cups 20 retain the lead screw for free rotation therein. In this embodiment of the invention the bottom bearing cup is located in a thrust pad-mounted spring 25. The height of the thrust pad 26 can be adjusted by a screw 27 to provide a desirable degree of end load on the lead screw 12.

Attached to the lead screw 12 is a nut 28 with a grooved bore 36 that interfits with the lead screw threading. The nut 28 is in the form of a collet 33 having sleeve portions 34 that extend upward from a body 32. Each of the sleeve portions 34 has a head 38, of a diameter greater than that of the body 32, that extends from an intermediate frusto-conical section 40.

The pitch of the lead screw 12 is such that the axial force on the nut 28 will provide axial displacement of the nut, with the lead screw rotating to accomodate such movement.

A thrust pad 54, with an interior threaded bore is threadably secured to the outer surface of the nut body 32. A compressed biasing spring 50 exerts a force between the thrust pad 54 and a pressure ring 52 positioned around the collet sleeve portions 34. The biasing spring 50, by exerting an upward force on the pressure ring 52, urges the sleeve portions 34 inward so as to apply friction fit between the nut 28 and lead screw 14. The degree of friction between the nut 28 and the lead screw 12 may be changed by adjusting the position of the thrust pad on the nut body 28 so as to adjust the force applied by the spring 50.

The electrode platform 58 is attached to the nut by a bayonet 56 that extends laterally outward from the thrust pad 54. The bayonet is positioned in a connecting slot 96 in the platform mounting arm 59, and held there by a set screw 72. Each of the electrode platform retaining bores 62 is provided with a friction clutch 68 to support electrode probes on the platform.

To use the electrode holder assembly 10 of this invention, an electrode 64, connected to the instrument 76, is inserted through one of the electrode mounting bores 62 of the electrode platform 58, and held in place by a friction clutch 68. A container 100, containing sample solution to be analyzed, is positioned under the platform. By manually applying a downward force on the platform, the operator causes the nut 28 to rotate in the direction corresponding to downward movement of the nut. The nut 28 and platform 58 thus move downward. When the electrode 64 reaches the desired vertical position, in the sample container 100, the operator lets go and downward movement stops. The operator needs only one hand to move the platform up or down; yet the nut 28 exerts enough friction force on the lead screw 12 to maintain the platform height at the level set by the operator.

When the test is completed, the operator applies an upward force on the platform 58 to retract the electrode from the container 100. Thus the operator can accurately position and reposition the electrodes with minimal effort.

Figure 3:
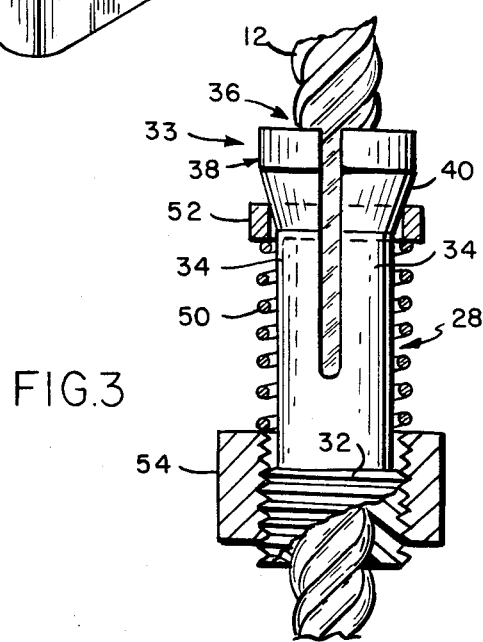
FIG. 3 is a a close up view of the adjustable bias nut of the preferred embodiment of this invention.

As seen in FIGS. 2 and 3, the nut 28 is designed to substantially eliminate any backlash of initial platform 58 adjustment. This is accomplished by the friction fit between the nut sleeve portions 34 and the lead screw 12. This friction serves a second purpose, namely, the retention of the platform position in the absence of operator-applied force. Thus the force exerted by bias spring 50 should be enough to provide this degree of friction, yet not so great as to unduly impede height adjustment by the operator. By adjusting the position of the thrust pad 54 on the nut body 32, the force exerted by the bias spring 50 can be adjusted so the friction fit of the collet heads 38 can be changed, as described above, to adjust for wear, or to accomodate different weights to be supported by the nut 28.

What is claimed as new and desired to be secured by Letters Patent of the United States is:

1. A test probe holder assembly for supporting at least one test probe so that the vertical position of the probe can be readily adjusted, said assembly comprising:
   (A) a frame;
   (B) a vertically aligned threaded lead screw with top and bottom ends and mounted to said frame at said top and bottom ends for free rotation;
   (C) a threaded nut assembly on said lead screw, the pitch of said nut and lead screw threading being such that a vertical force on said nut causes rotation of said lead screw and vertical movement of said nut;
   (D) a probe platform mounted to said nut so as to transfer externally applied forces to said nut so as to enable vertical movement of the platform relative to said lead screw, said probe platform having at least one probe mounting means for a test probe that extends downward therefrom; and
   (E) a friction force means attached to said nut for applying a friction force between said nut and said lead screw so as to maintain the vertical position of said probe platform relative to said lead screw in the absence of an externally applied force.

2. The test probe holder assembly of claim 1 further including means for applying an end load on said lead screw.

3. The test probe holder assembly of claim 2 wherein said means for applying an end load on said lead screw comprises: a vertically-adjustable thrust pad mounted to said frame beneath said lead screw bottom end; a spring located on said thrust pad; and a bearing cup located within the top of said spring, said lead screw bottom end retained within said bearing cup.

4. The test probe holder assembly of claim 1 wherein said nut assembly comprises a nut body with a bore, a threaded collet extending from said nut body threadedly engaging said lead screw, and means for compressing said collet against said lead screw to provide said friction force.

5. The test probe holder assembly of claim 1 wherein said nut assembly comprises:
a nut body with a threaded bore that fits said lead screw and a threaded outer surface; a collet comprising sleeve portions extending from said nut body, each of said sleeve portions having a head with a frusto-conical outer shape; a pressure ring disposed around said sleeve heads; a thrust pad threadably coupled to said nut body and a bias spring extending between said thrust pad and said pressure ring, so that said bias spring urges said sleeve portions inwardly against said lead screw to provide a friction fit between said nut assembly and said lead screw, the friction being adjustable by adjusting the position of said thrust pad on said nut body.

6. The test probe holder assembly of claim 1 wherein said nut assembly includes a laterally extending arm including a means for supporting said probe platform on said arm.

7. The test probe holder assembly of claim 6 wherein said lead screw and said nut assembly are disposed in a tower having wall means and base means, and said laterally extending arm for supporting said probe holder platform extends through an elongated vertical slot located in said tower wall means.

* * * * *